United States Patent
Zhao et al.

(10) Patent No.: US 8,294,094 B1
(45) Date of Patent: Oct. 23, 2012

(54) METHOD AND APPARATUS FOR REDUCING SUBSTRATE EDGE EFFECT DURING INSPECTION

(75) Inventors: Yan Zhao, San Jose, CA (US); Jack Jau, Los Altos Hills, CA (US); Yi-Xiang Wang, Fremont, CA (US)

(73) Assignee: Hermes Microvision Inc., Hsinchu (TW)

( * ) Notice: Subject to any disclaimer, the term of this patent is extended or adjusted under 35 U.S.C. 154(b) by 0 days.

(21) Appl. No.: 13/211,206

(22) Filed: Aug. 16, 2011

(51) Int. Cl.
*G01N 23/00* (2006.01)
*G21K 7/00* (2006.01)
(52) U.S. Cl. .................. 250/306; 250/307; 250/492.3
(58) Field of Classification Search .................. 250/306, 250/307, 309–311, 492.1, 492.2, 492.21, 250/492.22, 492.3
See application file for complete search history.

(56) References Cited

U.S. PATENT DOCUMENTS

| 6,903,338 | B2 | 6/2005 | Mankos et al. | |
|---|---|---|---|---|
| 7,884,334 | B2* | 2/2011 | Zhao et al. | 250/398 |
| 7,982,186 | B2* | 7/2011 | Kanai et al. | 250/306 |
| 2010/0258722 | A1* | 10/2010 | Fang et al. | 250/310 |
| 2010/0320381 | A1* | 12/2010 | Zhao | 250/307 |
| 2010/0327160 | A1* | 12/2010 | Zhao et al. | 250/307 |
| 2011/0036981 | A1* | 2/2011 | Zhao et al. | 250/307 |

\* cited by examiner

*Primary Examiner* — Bernard E Souw
(74) *Attorney, Agent, or Firm* — Stout, Uxa, Buyan & Mullins, LLP (57) ABSTRACT

An apparatus and method are introduced in this invention to reduce the edge effect of a substrate that causes image variation or distortion due to applied substrate bias. An edge plate with an edge effect eliminator are provided such that substrate is inspected by a charged particle beam can capture images without distortion at substrate edge.

26 Claims, 11 Drawing Sheets

METHOD AND APPARATUS FOR REDUCING SUBSTRATE EDGE EFFECT DURING INSPECTION

BACKGROUND OF THE INVENTION

1. Field of the Invention

The present invention relates to a charged particle beam inspection system, and more particularly to an apparatus and a method that reduce inspection image variation during inspection of a position near a substrate edge.

2. Description of Related Art

Figure 1:
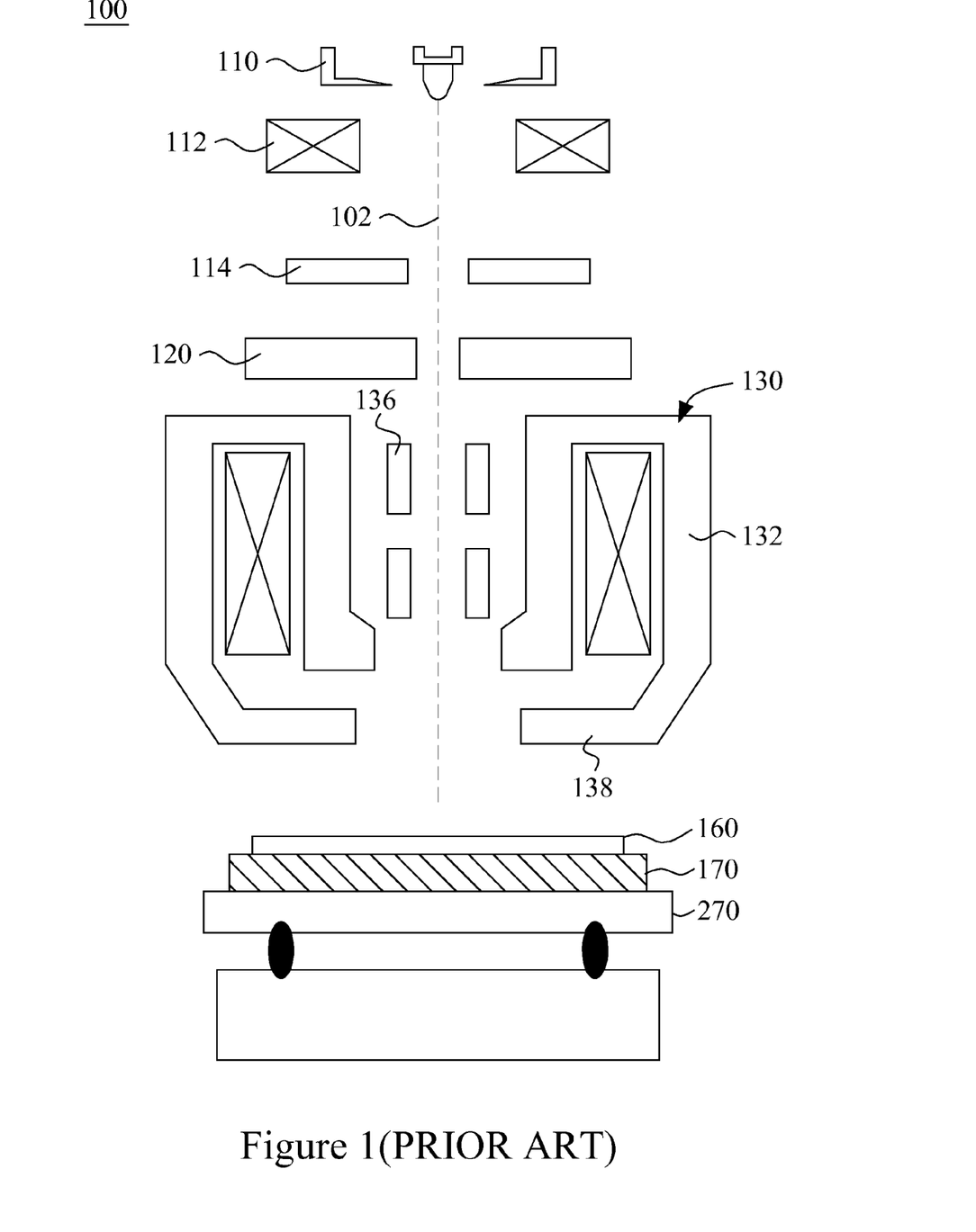
FIG. 1 is a schematic illustration of a representation of a conventional charged particle beam tool.

Fabrication of a semiconductor device, such as a logic or memory device, may include processing a substrate or wafer via any of various semiconductor processing tools. As feature size continuously shrinks, e.g., from 45 to 16 nm, use of the charged particle beam inspection tool becomes increasingly important for detecting abnormalities within the device at steps as early as possible. A conventional charged particle beam inspection tool 100 is shown in FIG. 1, which includes a charged particle emitter 110, a condenser lens 112, an aperture 114, an in-lens detector 120, an objective lens 130, and a substrate chuck (mechanical or electrical) assembly 170 mounted on an X-Y stage 270 to sustain a substrate 160. The imaging practice is irradiating a charged particle beam 102, to the surface of the substrate 160 and detecting the backscattered and secondary charged particles emanating from the surface of substrate 160. Detailed imaging practice is followed as that the primary charged particle beam 102 is emitted from the charged particle emitter 110, condensed by the condenser lens 112, and passed through the aperture 114. Then, the objective lens 130 will focus the primary charged particle beam 102 on to the surface of the substrate 160, and secondary charged particles are emanated from the surface of the substrate 160 to the in-lens detector 120. The objective lens 130 includes pole-piece 132, deflectors 136, and electrodes 138.

In order to perform a low energy inspection, a bias voltage is applied between the plate holding the substrate 160 and the objective lens 130. Since the substrate is not located in an area free of electrical fields, its material, shape and bias voltage may change the spatial electrical field distribution between the substrate 160 and objective lens 130. In general, the spatial electric field is substantially axial symmetrical with respect to the central beam, i.e., the central axis 102 of the assembly. This is essential for the charged particle beam to be focused into a small spot of round shape. However, when the edge peripheral portion of the substrate 160 is moved close to the central axis 102, the spatial electrical field distribution will become significantly non-axial symmetrical due to the bias voltage on substrate 160, discontinuity of the material and shape outside the substrate 160 and stage 170. The non-axial symmetrical distributed electric field shifts the incident primary charged particle beam, and will cause the obtained image varying from the expected in position, scaling, and focus, known as image shifting, distortion and defocus.

Figure 2A:
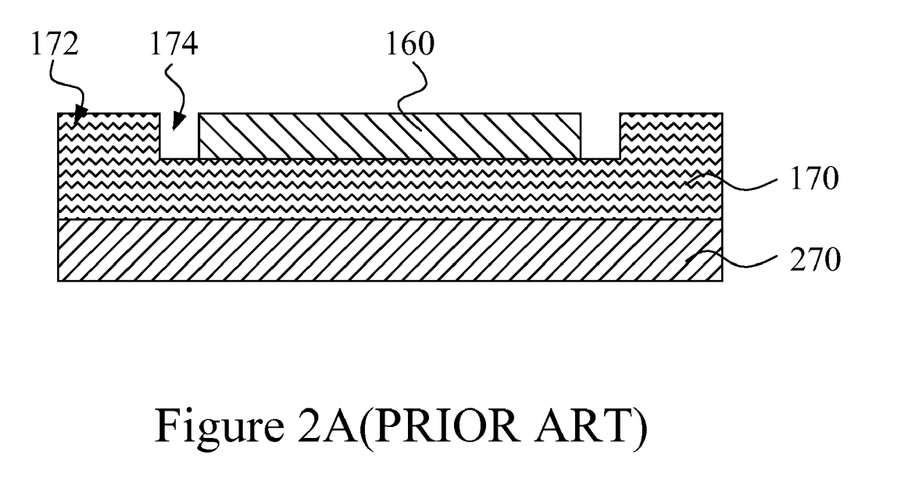
FIG. 2 is a schematic illustration of a representation of a conventional stage with a substrate thereon, wherein the stage has a concave region suitable to fit a substrate therein.
Figure 2B:
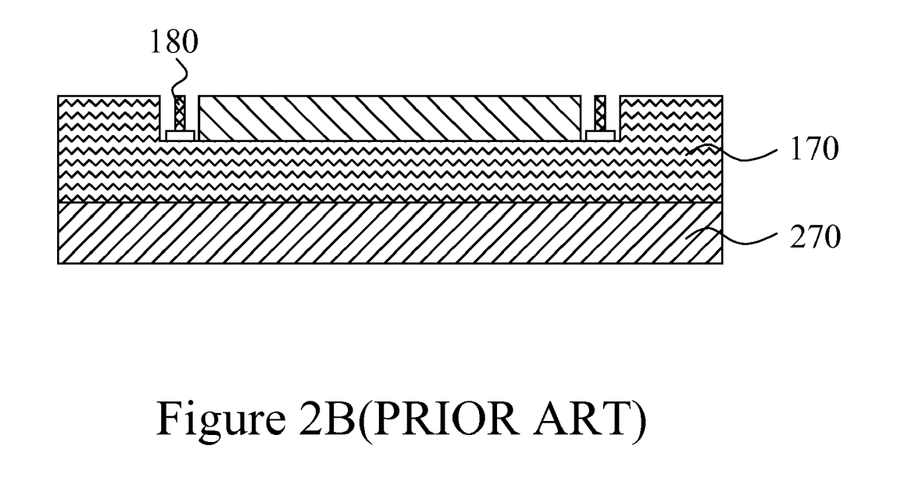

One conventional chuck assembly 170 for sustaining a substrate 160 is shown in FIG. 2A and FIG. 2B, wherein the chuck assembly 170 has a peripheral protruding region 172 to enclose the substrate 160. A small gap 174, which is most likely not equal around the chuck, is designed for tolerating the position accuracy when the substrate is loaded. Therefore, the gap will not form uniform electric field and the edge field effect will distort the primary beam due to the gap. In order to solve the edge effect issue, Mankos et al., as described in U.S. Pat. No. 6,903,338, provide a method to wear out the edge effect, as shown in FIG. 2B, wherein the gap 174 is increased for adopting an insert ring 180 and a voltage is applied to the insert ring 180 according to size of the gap 174 to reduce the edge effect during the inspection of the substrate edge.

However, the prior art of enlarged gap with inserted and biased ring 180 by Mankos et al. is impractical to implement. The height, shape and flatness of the ring 180 is too difficult to control by machining and assembly, and it also needs additional isolation inside the small gap from holder base 270 and wafer 160, where charged particle beam, either primary or secondary, is attached to the isolation, the insulation performance and charging effect may induce more severe problems to the tool.

The present invention provides another apparatus and method to reduce the substrate edge effect during patterned substrate inspection.

SUMMARY OF THE INVENTION

This invention provides a method for reducing edge effect of a substrate, which comprises steps of capturing a central image and a peripheral image of a patterned surface of the substrate by using a charged particle beam, and applying a voltage between the substrate and an edge plate enclosing the substrate, wherein a voltage is determined according to a difference between the central image and the peripheral image.

This invention also provides a system for reducing edge effect of a substrate during inspection, which comprises an inspection tool with a charged particle beam as a probe, a substrate holding device with an edge plate enclosing the substrate, and means for applying a voltage between the edge plate, wherein the voltage is determined by a difference between a central image and a peripheral image of a patterned surface of the substrate, at targeting locations, wherein the central image and the peripheral image are captured by the same inspection tool for inspection.

This invention further provides a method for reducing edge effect of a substrate during inspection, which comprises steps of pre-scan or irradiate a surface of the substrate with a charged particle beam to achieve a certain level of a surface charging, capturing a central image of the surface of the substrate by using the charged particle beam, capturing a peripheral image of the surface of the substrate by using the charged particle beam, determining a voltage between an edge plate and the substrate according to a difference between the central image and the peripheral image, and applying the voltage to the edge plate enclosing the substrate.

Other advantages of the present invention will become apparent from the following description taken in conjunction with the accompanying drawings wherein are set forth, by way of illustration and example, certain embodiments of the present invention.

DETAILED DESCRIPTION OF EXEMPLARY EMBODIMENTS

Various example embodiments of the present invention will now be described more fully with reference to the accompanying drawings in which exemplary embodiments of the invention are shown. In the drawings, thicknesses of layers and regions may be exaggerated for clarity.

Detailed illustrative embodiments of the present invention are disclosed herein. However, specific structural and functional details disclosed herein are merely representative for purposes of describing exemplary embodiments of the present invention. This invention may be embodied in many alternate forms and should not be construed as limited to only the embodiments set forth herein. For example, this invention is mainly applied to wafer substrates used in semiconductor device fabrication. Yet, the substrate can also be photo-mask substrate of round or square shape where edge field effect exists.

Accordingly, exemplary embodiments of the invention are amenable to various modifications and alternative forms, embodiments herein being shown by way of example in the drawings and description. It should be understood, however, that there is no intent to limit example embodiments of the invention to the particular forms disclosed, but on the contrary, exemplary embodiments of the invention are to be construed as covering all modifications, equivalents, and alternatives falling within the scope of the invention. Like numbers refer to like elements throughout the description of the figures.

An ordinary charged particle beam inspection tool includes a charged particle source for emitting a primary charged particle beam that passes through one or more of a condenser lens, an aperture, an objective lens, an in-lens deflector, to be converged into a detecting probe and scanned over a surface of a substrate which is sustained by a chuck mounted on a movable stage. The irradiation of the primary charged particle beam on the substrate surface produces secondary charged particles which are collected by detector and is processed to form an image of the scanned area.

In order to perform low energy inspection and reduce radiation damage of to the patterns/devices on the surface of substrate, the substrate is negatively biased to −V volt with respect to the grounded final objective lens (0V) such that the primary charged particle beam will suffer a regarding force to lose its energy while traveling to the substrate surface. In this case, the substrate is immersed in an electrical-field region; therefore the spatial field distribution above the substrate surface is very critical to the focus and landing position of the primary charged particle beam. While the primary charged particle beam irradiates to the locations in inner portion of substrate, the equipotential lines along path of the charged particle beam are substantially axial symmetrical distributed between the substrate and the pole piece of the objective lens. In terms of electrical field E, there is only a vertical component Ez pointing from pole piece to substrate surface. However, while the primary charged particle beam irradiates to the locations near the edge of the substrate, the spatial distribution of the electric field above the surface become significantly axial asymmetrical due to material, structural or topographical change of the substrate, besides the vertical component Ez, there will be a lateral component Er significant enough to cause image shift, distortion and defocus.

Besides the material and structural factors that contribute to the axial asymmetrical field distribution near the edge of the substrate, the surface charging condition of the substrate may also deteriorate the edge effect. For enhancing certain types of electrical defects, such like open circuit or short circuit, it is often necessary to charge the substrate to positive or negative by pre-irradiating (flooding) with charged particle beam before inspection. According to Zhao et al. (US 20080296496; "Method and apparatus of wafer surface potential regulation"), the substrate surface can be charged to a negative or positive potential with respect to biased substrate. It is observed that this kind of processing may deteriorate the edge effect and enlarge the edge effect zone, thus the present invention can also be used to cancel or minimize these adverse impacts according to the surface charging level.

Figure 3A:
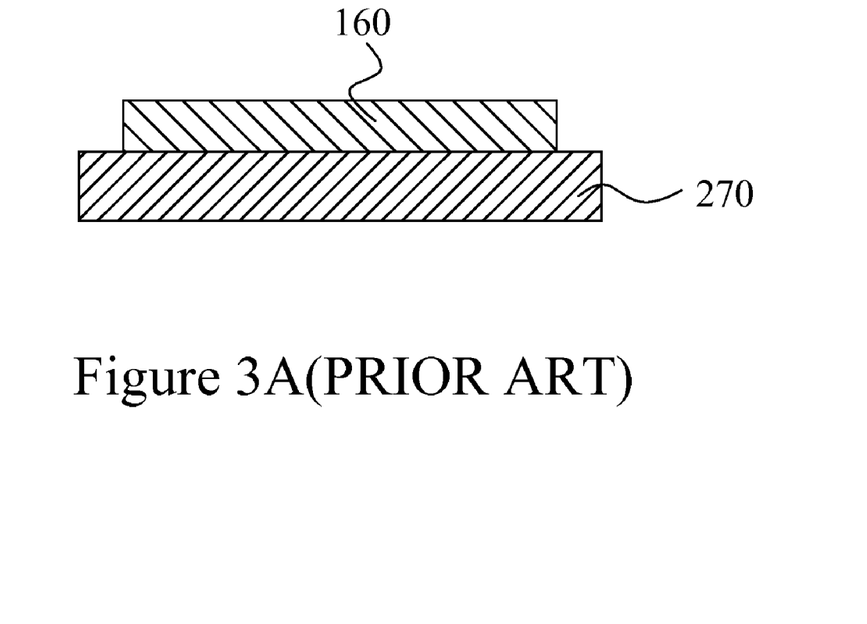
FIG. 3 is a schematic illustration of a representation of another conventional stage with a substrate thereon, wherein the stage is planar without protrusion peripheral.
Figure 3B:
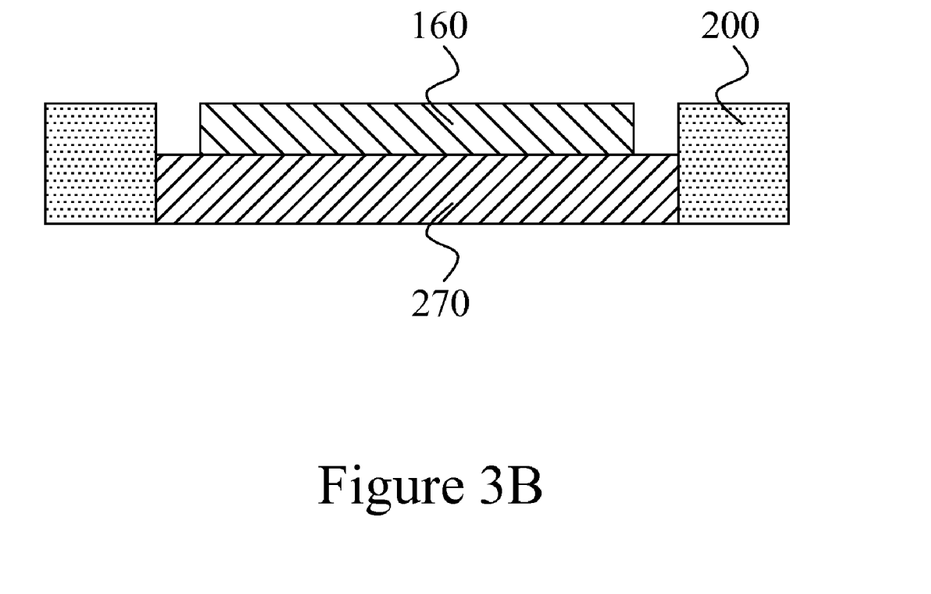

For widely used planar substrate holding plate 270 as shown in FIG. 3A, the substrate 160 will incur more severe edge effect due to there is no peripheral protruding region to elevate the dropping field outside edge. Therefore, in one embodiment of this invention, an edge plate 200 has to be configured to encompass the peripheral of the substrate 160, as shown in FIG. 3B. Further embodiments will all be based on this basic configuration.

Figure 4A:
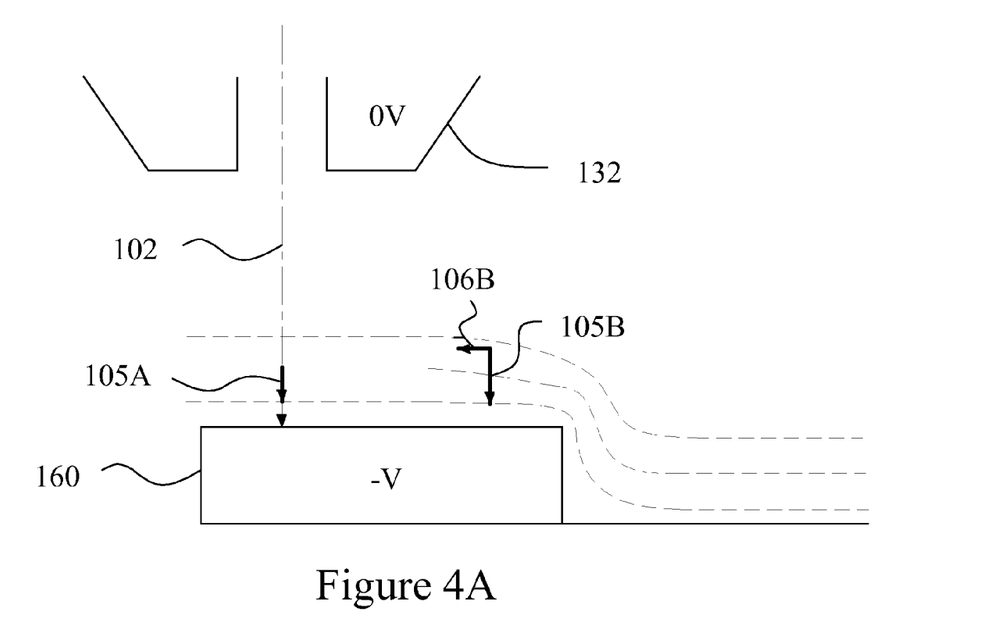
FIG. 4 is a schematic illustration of a primary charged particle beam emitting on central portion of a substrate and substrate edge.
Figure 4B:
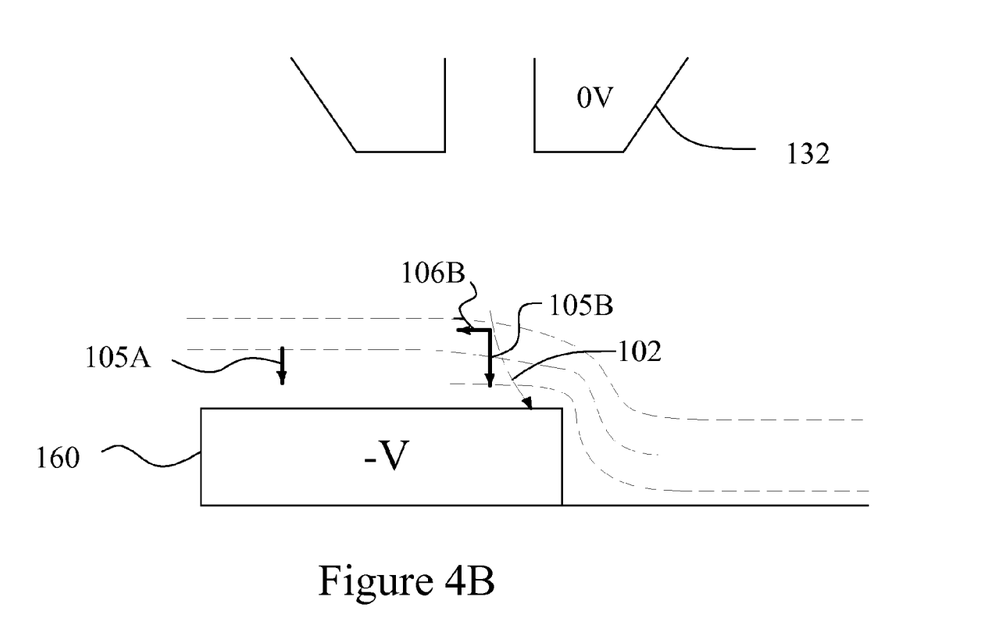
Figure 4C:
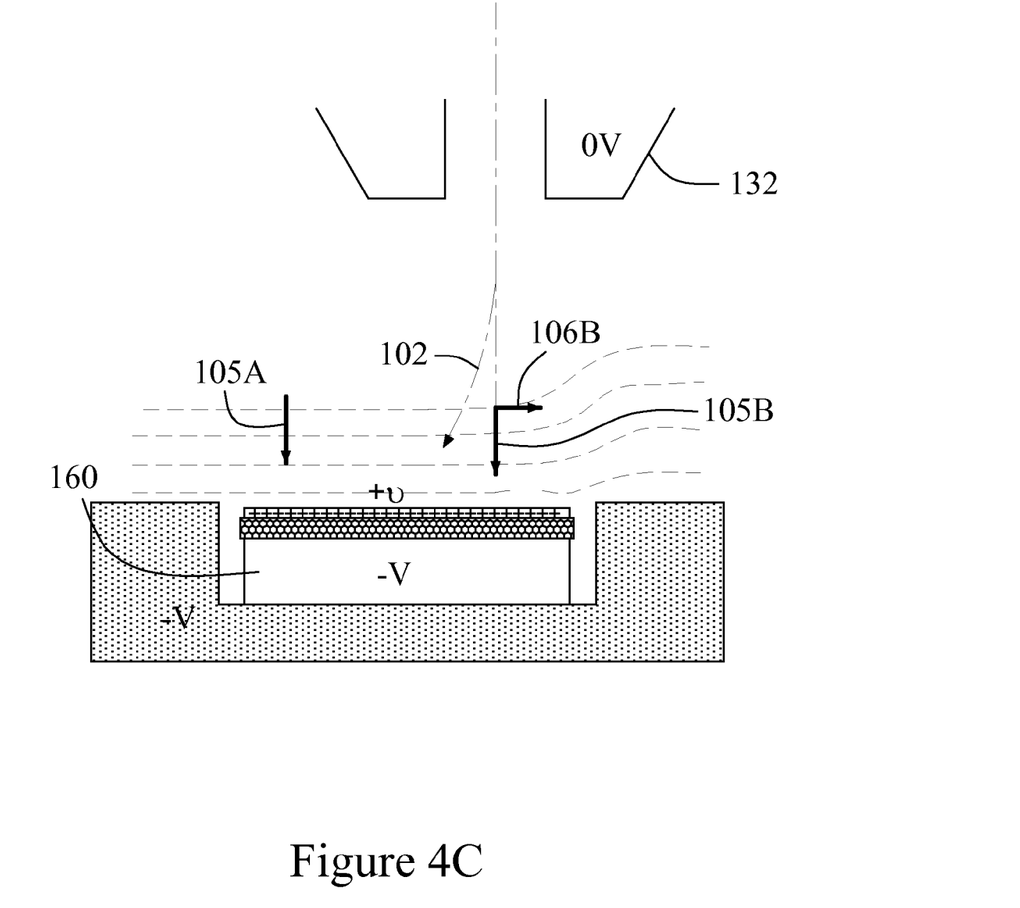

FIGS. 4A and 4B illustrate a primary charged particle beam acting differently from a central portion of the substrate 160 to the peripheral or edge portion of the substrate 160. The central primary charged particle beam 102, as shown in FIG. 4A, from the pole-piece 132 with 0V potential, will strike vertically to the substrate 160 biased −V at central portion or far away from edge of the substrate 160, as it mainly suffers an axial symmetrical field, $E_z \neq 0$ (105A) and $E_r = 0$ (not shown in the figure). However, when inspecting the edge portion of the substrate, the central primary charged particle beam 102 will experience an axial asymmetrical field. The equal potential lines between the lens pole piece and substrate will conform to sectional shape of the substrate 160 (assume substrate is conductive), the lateral electrical field component $E_r$ (106B) is no longer ignorable along the central axis. The primary charged particle beam 102 traveling along the central axis will suffer an off-axis deflection force, and be shifted away from its targeting position on the substrate 160, as shown in FIG. 4B. Edge effect will also change axial filed component $E_z$. As seen from FIG. 4, $E_z$ near the edge 105B of substrate will also be different from 105A at the center. If the difference is significant enough, the image focus near substrate edge will differ from that of center. FIG. 4C shows another case where substrate surface is pre-charged (flooded) positively +υ with a charged particle beam before inspection imaging. If the surface charging is higher than the surroundings at the same plane, the distortion and shifting will be opposite. Hence, the image distortion may include stretch or contract. Referring to FIG. 4C, while the potential on the substrate 160 is −V+υ and higher than the peripheral −V, the primary charged particle beam 102 now will be deflected inwards. Though mentioned above are the distortion or shifting of image due to the additional horizontal component induced due to the edge, there is also another impact of edge effect, which will cause image defocus due to the axial field component change between the central and edge portion of the substrate.

Two measures can be used to change the edge field distribution, which include the use of a conductive plate and a bias voltage applied to the conductive plate. The conductive plate elevates the equal potential lines near substrate edge to the similar level as that of inner location, such that the gradient of potential in the direction parallel to surface, or lateral component of electrical field, is minimized to substantially zero.

Since the height of conductive plate to substrate surface and the gap between substrate and conductive plate cannot be controlled precisely to be the same everywhere around substrate, the electrical field at the points of the same radial distance to the edge will not be the same at all the angular direction. In one embodiment, a variable bias voltage can be further used to compensate these edge field variation from place to place in accordance with the deference observed from image and measured as position shift, scaling and/or focus variation.

Figure 5A:
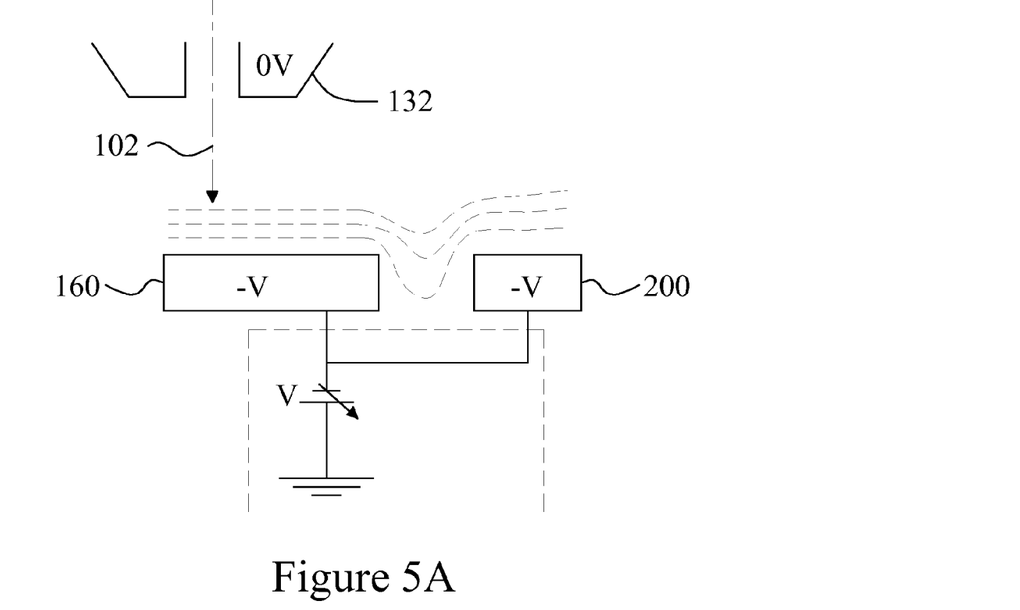
FIG. 5 is a schematic illustration of an edge effect eliminator applied to an edge plate to reduce edge effect of a substrate in charged particle beam inspection in accordance with an embodiment of the present invention.
Figure 5B:
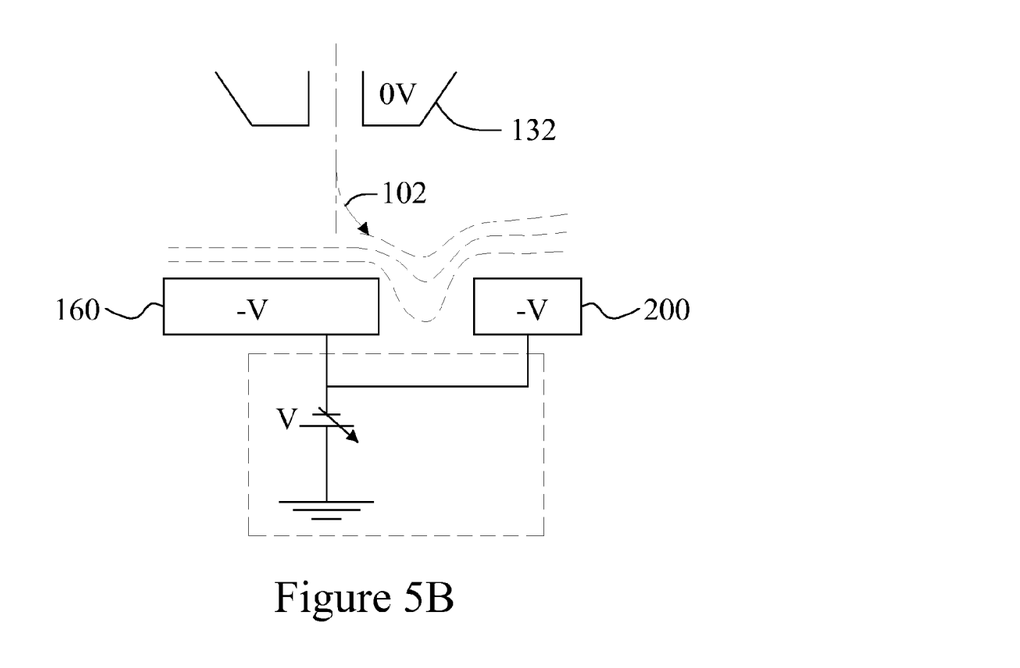
Figure 5C:
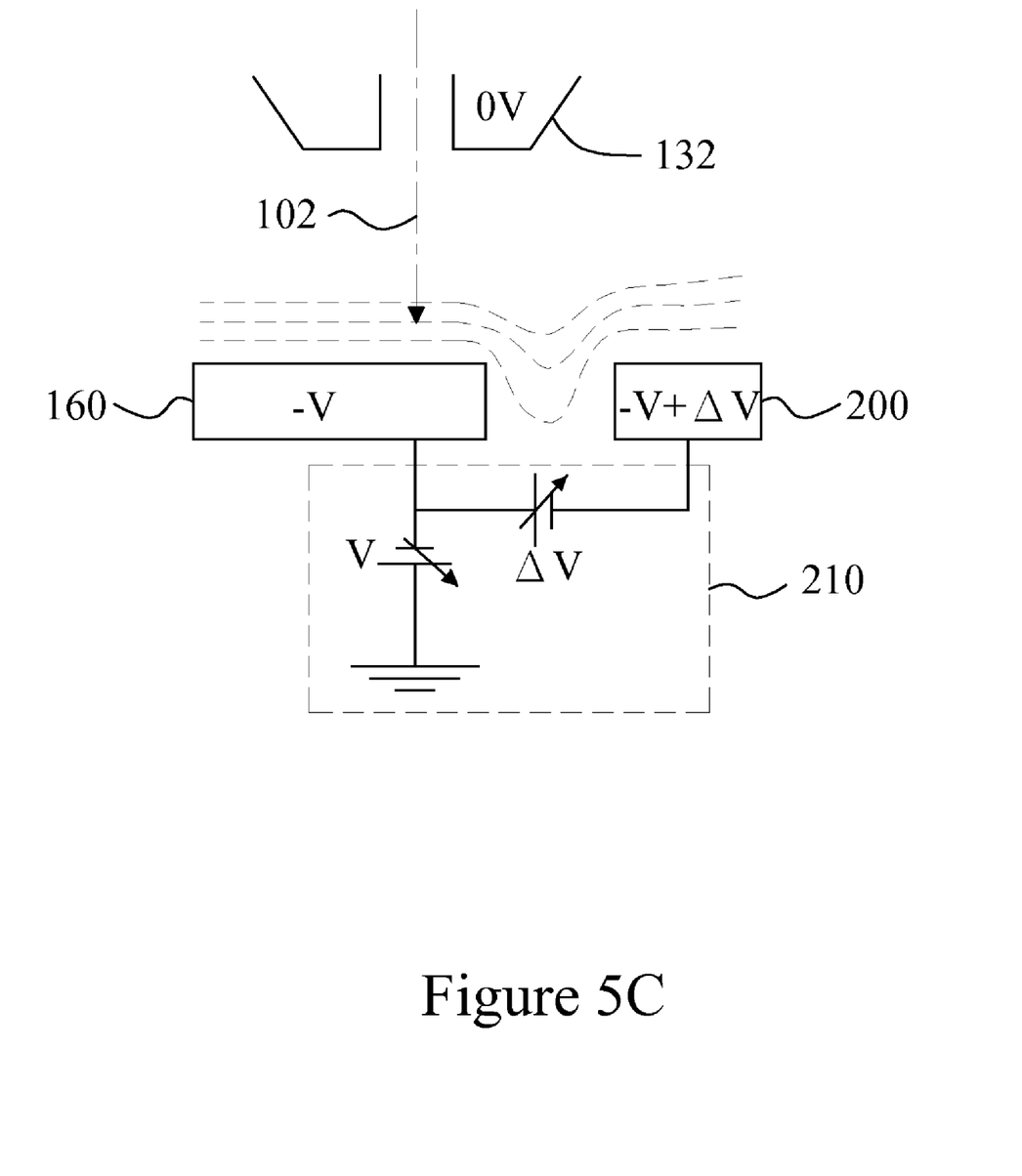

Turning to FIG. 5A, FIG. 5B, and FIG. 5C, though position shift distance is used to illustrate the impact of asymmetrical field at an edge portion of substrate here, it also being understood and applicable to other measurable parameter from image comparison, including image scaling factor and focus (current or voltage) variation. In the present invention, an edge plate 200 is configured to enclose the substrate 160 to smoothen potential variation at the edge of the substrate 160. In FIG. 5A, the edge plate 200, which is generally a circular plate when the substrate 160 is round, is configured near edge of the substrate 160 and encompassing the substrate 160. If the substrate 160 is square, such as mask or reticle, the edge plate 200 may have a square frame outline. However, potential distribution at a gap between the substrate 160 and the edge plate 200 still varies with a drop down, as shown in FIG. 5B. When the primary charged particle beam 102 moves to edge of the substrate 160, it still deflects due to the drop down potential distribution, and inspected image still has distortion, scaling or defocus issue which depends on the extent of edge effect.

One embodiment of the present invention, as shown in FIG. 5C, introduces an edge effect eliminator 210. The edge effect eliminator 210 adjustably add ΔV bias voltage on top of the stage bias voltage (−V). This procedure adjusts the equipotential lines of the electrical field near substrate 160 edge peripheral position to compensate the height variation between substrate 160 surface and edge plate 200, as well as potential difference between edge plate 200 and substrate 160 surface due to charging. A relatively flat equipotential line distribution throughout the substrate surface will produce non-distorted or non-defocused inspection image during inspection.

In another embodiment, if the substrate surface potential varies with different process steps, or even pre-charged by flood process, a variable bias voltage can also be applied to the conductive plate to change the edge field distribution in accordance with the substrate surface charging status. The exist and bias of the conductive plate enclosing the substrate will not change or alter the uniformity of field distribution at center or inner portion of substrate, but near substrate edge peripheral portion, so the field distribution or equal potential line can be planarized according to the beam position by properly biasing the conductive edge plate. The central primary charged particle beam near the edge position is pushed less outward or inward due to the improved axial symmetrical field between substrate surface and pole piece of objective lens.

Also referring to FIG. 5C, stage is bias to −V with respect to ground by a power supply. In order to compensate the image difference (for instance, shift) between edge area and center area, an additional power supply with voltage V, provided by edge effect eliminator 210, should be applied between substrate 160 and the edge plate 200 to modulate the potential distribution such that the central primary charged particle beam 102 can bombard straight forward to the substrate 160 without deflection. The edge effect eliminator 210 comprises two power sources, one coupled between the substrate 160 and ground for −V bias voltage, the other coupled between the substrate and the edge plate 200 for $^\Delta$V bias voltage. The bias voltage $^\Delta$V can be positive or negative to meet different situations of substrate surface charging and edge plate height. The main purpose of the edge plate 200 and the edge effect eliminator 210 are configured to planarize potential distribution over an enlarged area of the substrate 160.

Figure 6A:
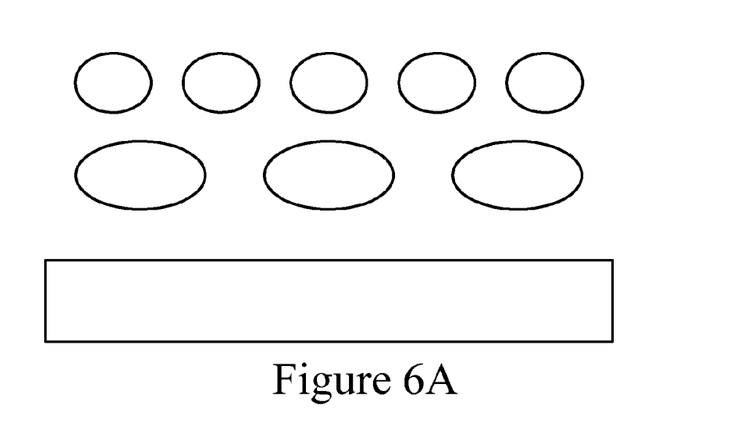
FIG. 6 is a schematic illustration of the same pattern on two scanned images acquired from central portion and edge portion of a substrate without any correction to the substrate edge, wherein a shift can be calculated.
Figure 6B:
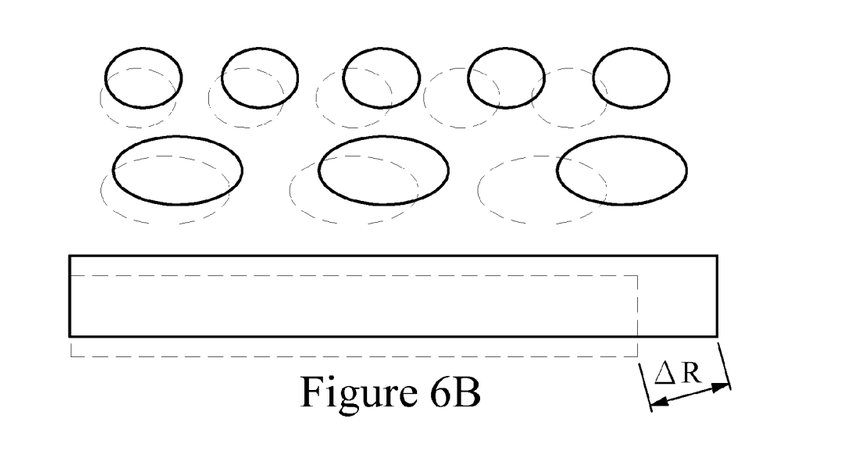
Figure 6C:
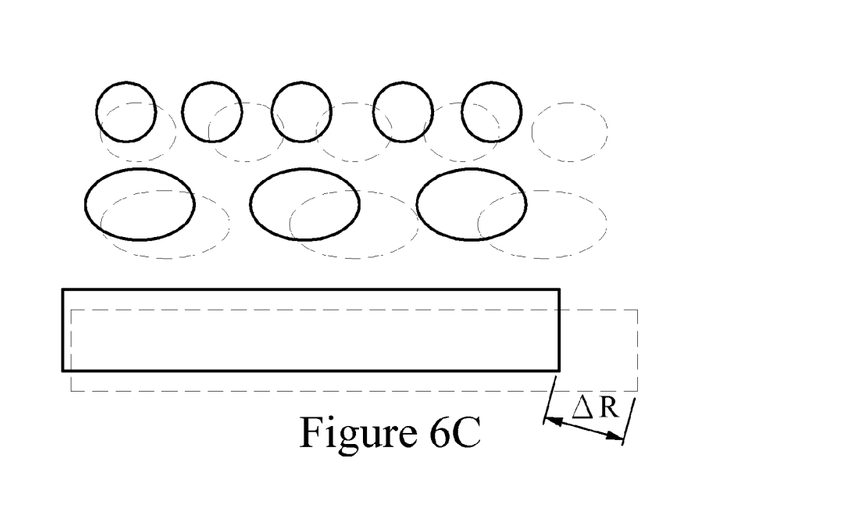

FIGS. 6A and 6B show two images captured from two dies at the same corresponding locations within the die (same location in die coordinate) in a patterned substrate. FIG. 6A captured is from a die located at the central portion of substrate, which will be served as an edge-effect-free reference image. FIG. 6B (solid line pattern) is captured from a die at the peripheral portion of substrate, say at distance R from substrate center. The edge-effect-free image is also drawn in FIG. 6B in dotted line for comparison. There is a shift of $^\Delta$R between these two images (positions) due to edge effect. The shift direction can be outward or inward; i.e., R can be in positive or negative value. Positive $^\Delta$R suggests a stretch distortion or outward shift in image due to potential of the substrate surface is lower than that of the conductive plate, while the negative $^\Delta$R suggests a contract distortion or inward shift due to the potential of the substrate surface is higher than that of the conductive plate, as shown in FIG. 6C.

Figure 7A:
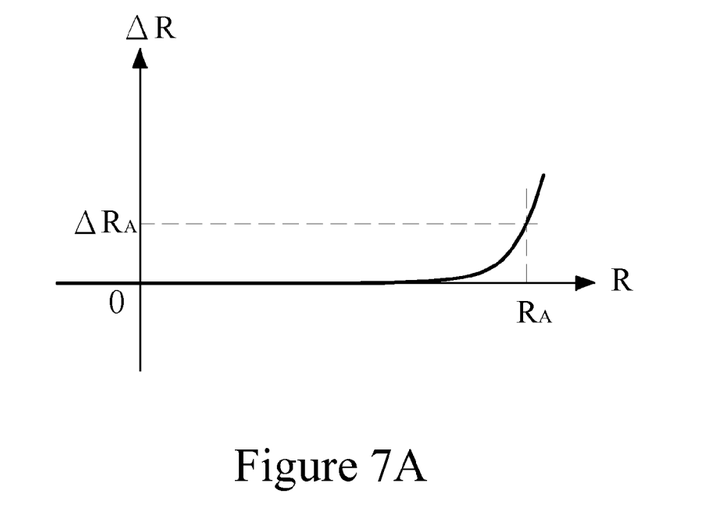
FIG. 7 is a schematic illustration of a relationship between the applied potential to the edge plate versus pattern shift as shown in FIG. 6.
Figure 7B:
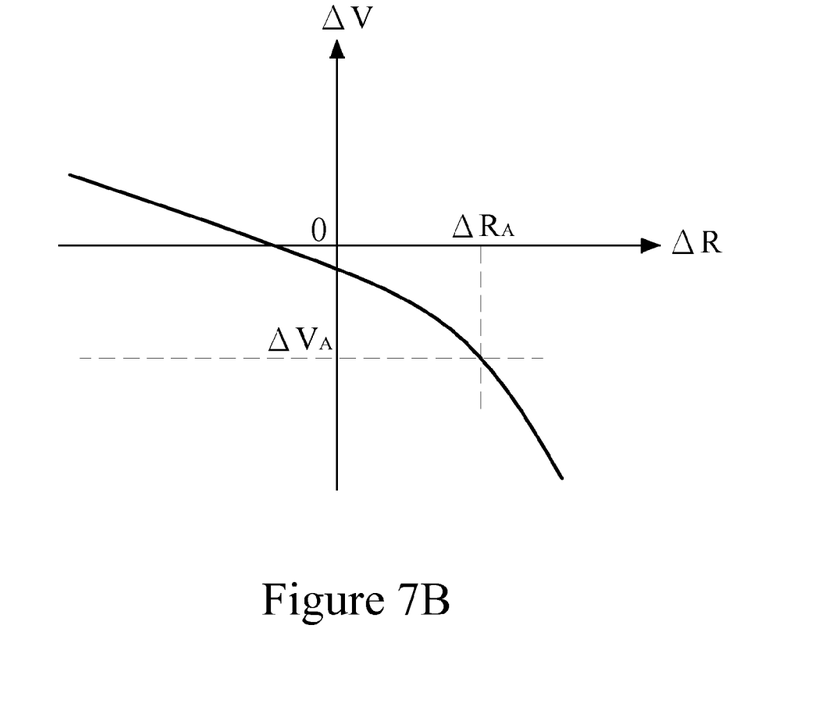

The biasing voltage $^\Delta$V for compensating the corresponding $^\Delta$R shifting can be measured and determined experimentally. A curve or a table can be established before inspection. FIG. 7A shows the position shift $^\Delta$R of images as a function of imaging location (x, y) or (r,θ) along a given axial or radial direction towards edge gap. Scaling of image and focus changes of image can also be measured and used as an indication of proper bias voltage. FIG. 7B shows the bias voltage needed to correct the corresponding position shift due to edge effect along that particular path. This value can be predetermined experimentally by searching the bias voltage until $^\Delta$R decrease to zero or a tolerable level. In general, each time substrate may be loaded with slightly position shift with respect to the plate, so the gap will not be equal and varies from loading to loading, thus a table, as shown in table 1 for example, needs to be established to record the changes of images at different positions, and corresponding bias voltage required for correcting such difference on various positions of the substrate area. In table 1, the image position is present in, but not limited to, R and coordinate system. The value should be read as bias voltage of corresponding position. Based on this table, bias voltage for correcting image difference at any position due to edge field effect can be looked up or interpolated from the table.

Table 1 Bias voltage required for correcting image difference due to edge field effect at various locations of substrate.

| R | θ | | | | | | | | |
|---|---|---|---|---|---|---|---|---|---|
| | 0 | 45 | 90 | 135 | 180 | 225 | 270 | 315 | 360 |
| 0 (reference) | 0 | 0 | 0 | 0 | 0 | 0 | 0 | 0 | 0 |
| 140 | 2 | 1.5 | 1.8 | 2 | 1.8 | 2 | 1.6 | 2 | 1.3 |
| 145 | 8.5 | 6 | 7 | 9 | 8 | 8 | 6 | 8.5 | 7 |
| 148 | 11 | 8.5 | 9 | 11 | 11 | 12 | 8.5 | 11 | 9 |

This invention also provides a method to learn bias voltage for all peripheral areas according to an embodiment of the present invention. The method to eliminate edge effect during inspection is as following: (1) acquiring the first image at a reference point inside a die at center portion of the substrate; (2) acquiring the second image at the same reference point but of a different die at peripheral portion of the substrate; (3) comparing the two images and calculate amount of difference measured as position shifting, or distortion scaling or defocus; (4) adjusting the bias potential applied to the edge plate through the edge effect eliminator until the amount of differences at each reference point is offset; (5) repeating steps (1) to (4) for a number of tabulated points over the area to be inspected; (6) storing the compensation factors (voltages) of each point to the inspection control computer; and (7) while imaging edge area for inspection, looking up the bias voltage by extrapolation or interpolation from the table based on the position, then applying the bias voltage to the charged particle system. In a more general inspection practice, the bias voltage can be applied automatically from position to position (regardless edge or center) while inspecting a substrate. Or, in manual operation, the amount of bias voltage applied to the edge plate may be determined by the inspection tool operator.

Figure 8:
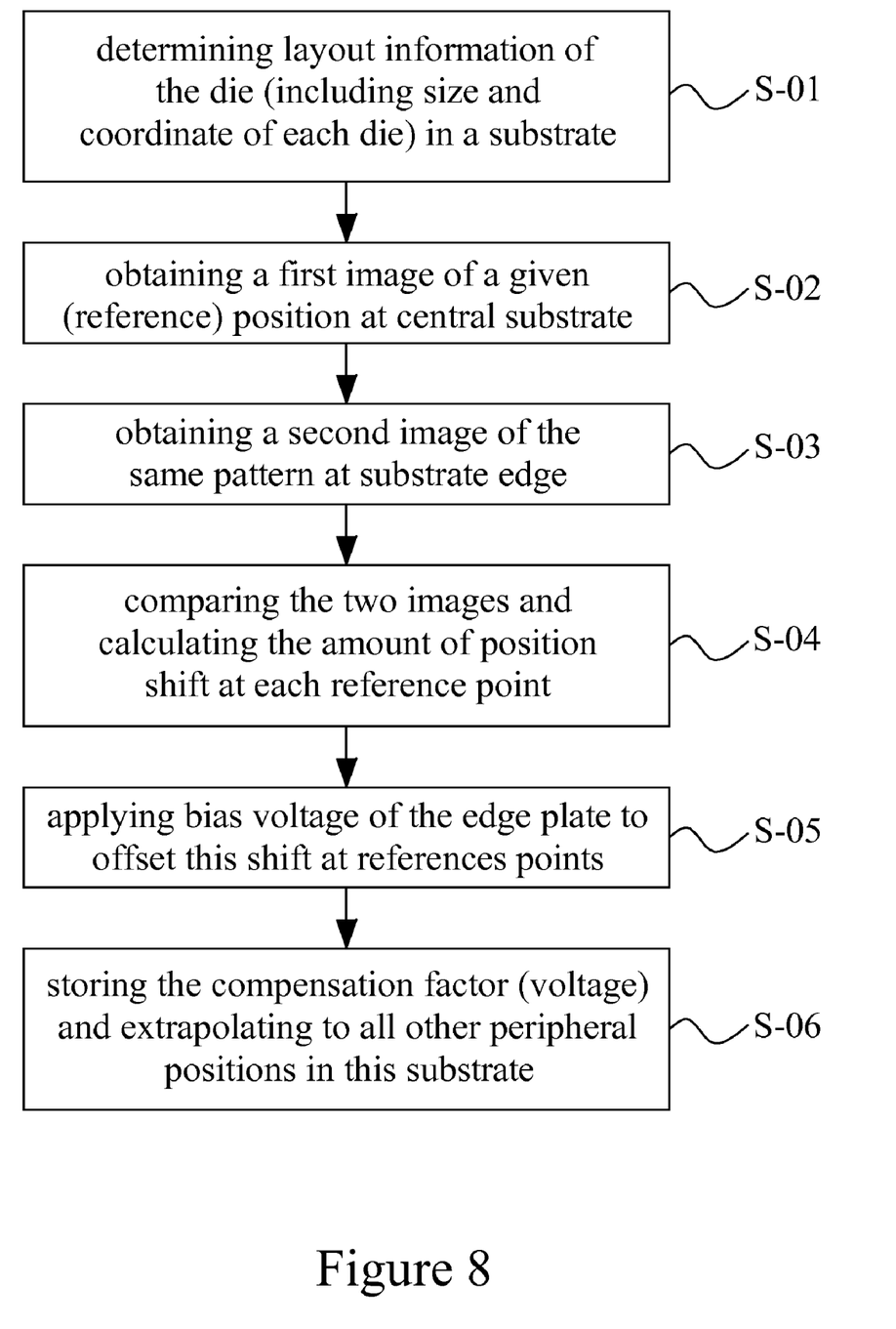
FIG. 8 is a flow chart showing the potential applied to the edge plate to offset the edge effect.

Referring to FIG. 8, a method of this invention is provided for reducing edge effect of a semiconductor substrate. First, layout information of the die (including size and coordinate of each die) in a substrate is determined (step S-01). Before scanning the substrate, an optional step of flooding the substrate surface can be performed. Then, a first image of a given (reference) position at central substrate is obtained by using a charged particle beam tool to scan it (step S-02). In this step, a pattern is chosen in a central die to be scanned. This first image is used for reference as a normal pattern. Next, a second image of the same pattern at substrate edge, or edge die, is obtained by using the same charged particle beam tool to scan the pattern at edge die (step S-03). In this step, the same pattern in edge die is chosen. Then, the two images can be compared to calculate the amount of position shift at each reference point of the pattern (step S-04). After calculating the image differences, for example, position shift, bias voltage of the edge plate is applied to offset this shift at references points of the pattern (step S-05). In this step, after applying bias potential to the edge plate, step S-03 is processed again to obtain another image, and step S-04 is performed again to check if there is any position shift at the reference points. Then, the compensation factor (voltage) is then stored and this factor is used to extrapolate to all other peripheral positions in this substrate (step S-06). In some instances, such an extrapolation can be used as a reference because every region in the peripheral portions of a substrate may have variant topography.

Figure 9:
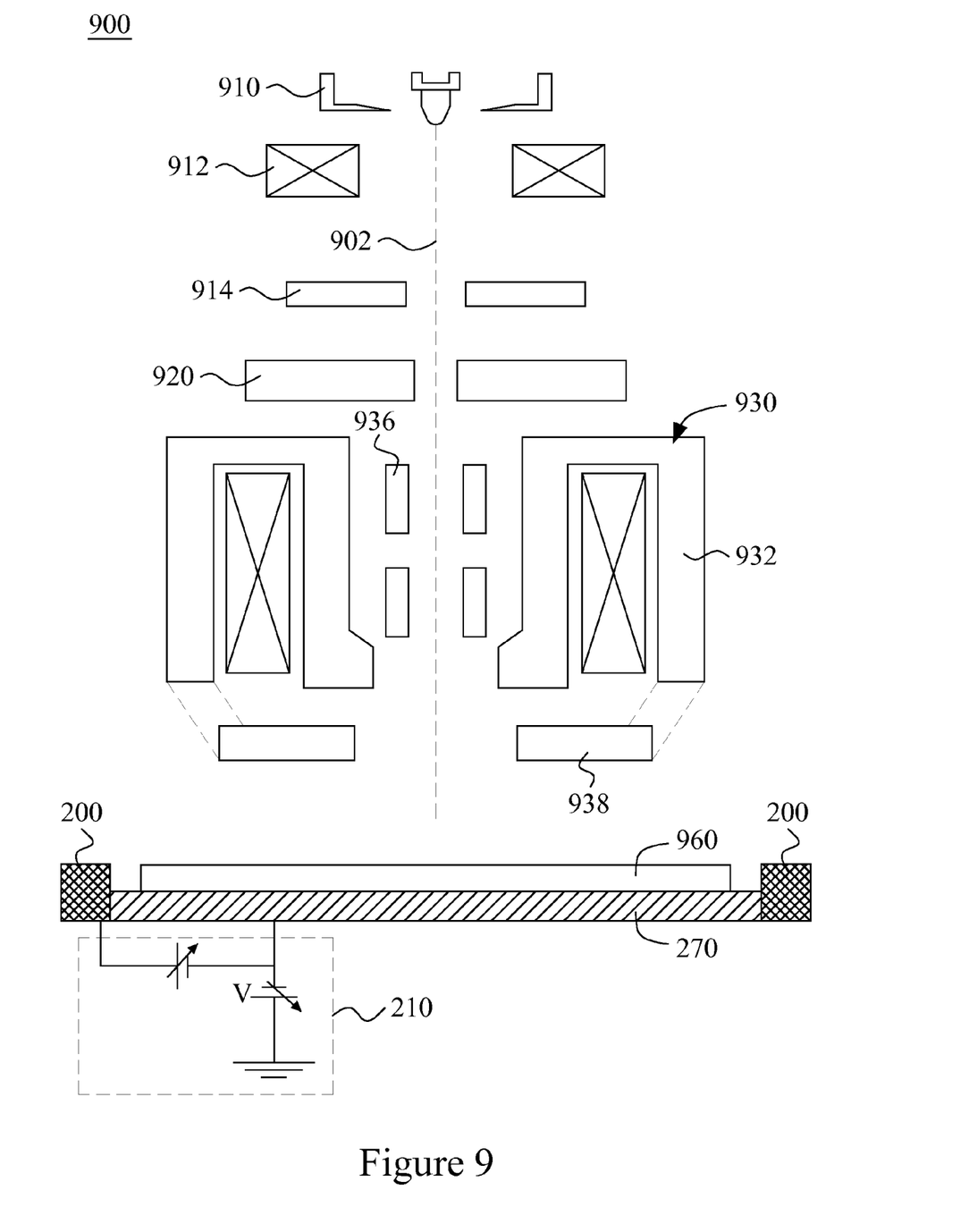
FIG. 9 is a schematic illustration of a charged particle beam tool with an edge plate encompassing substrate and an edge effect eliminator applied to the charged particle beam tool in accordance with an embodiment of the present invention.

Referring to FIG. 9, a charged particle beam tool 900 is provided, which comprises a charged particle source 910 for emitting a primary charged particle beam 902 through a condenser lens 912, an aperture 914, an in-lens detector 920, an objective lens 930, an in-lens deflector 936 to a substrate 960. The substrate 960 is bombarded by the primary charged particle beam 902 and then secondary charged particles are emanated from the substrate 960 surface to the in-lens detector 920. The substrate 960 is mounted on a stage 270 with an edge plate 200 surrounding the substrate 960. The edge effect eliminator 210 is provided to the edge plate 200 for providing a compensation potential such that potential distribution is uniform at the substrate edge.

After the edge effect eliminator 210 providing $^\Delta$V to the edge plate 200, potential distribution will be more uniform, or more planar at substrate edge and the primary charged particle beam emitting to the substrate will not be deflected or will be less deflected such that scanned image meets inspection requirement. Thus, defect inspection can be very accurate to conventional inspection.

Although the present invention has been explained in relation to its preferred embodiment, it is to be understood that other modifications and variation can be made without departing from the spirit and scope of the invention as hereafter claimed.

What is claimed is:

1. A method for reducing edge effect of a substrate, comprising steps of:
   capturing a central image and a peripheral image of a patterned surface of the substrate by using a charged particle beam; and
   applying a voltage between the substrate and an edge plate enclosing the substrate, wherein the voltage is determined according to a difference between the central image and the peripheral image.

2. The method of claim 1, wherein the edge plate is conductive with a top surface thereof substantial in the same height as the surface of the substrate.

3. The method of claim 1, wherein a polarity of the voltage can be positive or negative correlated to a level of differences between the central image and the peripheral image.

4. The method of claim 3, wherein a value of the voltage is proportional to the level of differences between the central image and the peripheral image.

5. The method of claim 4, wherein the peripheral image differs from the central image in a level of distortion measured by a scaling factor.

6. The method of claim 4, wherein the peripheral image differs from the central image in a level of shifting measured by an offset distance.

7. The method of claim 4, wherein the peripheral image differs from the central image in a level of focus measured by a focus current/voltage change.

8. The method of claim 1, further comprising a step of flooding the surface of the substrate before the capturing step.

9. A system for reducing edge effect of a substrate during inspection, comprising:
   an inspection tool with a charged particle beam as a probe;
   a substrate holding device with an edge plate enclosing the substrate, said substrate holding device for holding a substrate; and
   means for applying a voltage between the substrate and the edge plate, wherein the voltage is determined by a difference between a central image and a peripheral image of a patterned surface of the substrate at targeting locations, wherein the central image and the peripheral image are captured by the same inspection tool for inspection.

10. The system of claim 9, wherein the edge plate is conductive with a top surface thereof substantial in the same height as the surface of the substrate.

11. The system of claim 9, wherein the peripheral image has distorted patterns compared to the central image.

12. The system of claim 9, wherein the peripheral image has shifted patterns compared to the central image.

13. The system of claim 9, wherein the peripheral image has defocused patterns compared to the central image.

14. The system of claim 9, wherein the voltage is determined by a level of distortion measured by a scaling factor between the central and the peripheral images.

15. The system of claim 9, wherein the voltage is determined by a level of shifting measured by a distance between the central and the peripheral images.

16. The system of claim 9, wherein the voltage is determined by a level of defocus measured by a focus current/voltage change between the central and the peripheral images.

17. The system of claim 9, wherein a polarity of the voltage can be positive or negative determined by a level of difference between the central and the peripheral images.

18. The system of claim 9, wherein the inspection tool is a charged particle beam inspection tool.

19. A method for reducing edge effect of a substrate during inspection, comprising steps of:
    pre-scan or irradiate a surface of the substrate with a charged particle beam to achieve a certain level of a surface charging;
    capturing a central image of the surface of the substrate by using the charged particle beam;
    capturing a peripheral image of the surface of the substrate by using the charged particle beam;
    determining a voltage between an edge plate and the substrate according to a difference between the central image and the peripheral image; and
    applying the voltage to the edge plate enclosing the substrate.

20. The method of claim 19, wherein the surface charging can be positive or negative.

21. The method of claim 19, wherein the edge plate is conductive with a top surface thereof substantial in the same height as the surface of the substrate.

22. The method of claim 19, wherein a polarity of the voltage is positive or negative correlated to measures of a difference between the central and the peripheral images.

23. The method of claim 22, wherein a value of the voltage is proportional to the measures of the difference between the central and the peripheral images.

24. The method of claim 22, wherein the difference between the central and the peripheral images is of distortion measured by a scaling factor.

25. The method of claim 22, wherein the difference between the central and the peripheral images is a position shift measured by a distance.

26. The method of claim 22, wherein the difference between the central and the peripheral images is a focus change measured by a focus current/voltage.

* * * * *